(12) United States Patent
Biris et al.

(10) Patent No.: US 8,576,394 B2
(45) Date of Patent: *Nov. 5, 2013

(54) METHODS OF FABRICATING SURFACE ENHANCED RAMAN SCATTERING SUBSTRATES

(75) Inventors: Alexandru S. Biris, Little Rock, AR (US); Abhijit Biswas, Norman, OK (US); Ilker S. Bayer, Champaign, IL (US); Lloyd A. Bumm, Norman, OK (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/204,604

(22) Filed: Aug. 5, 2011

(65) Prior Publication Data

US 2011/0285992 A1 Nov. 24, 2011

Related U.S. Application Data

(63) Continuation of application No. 12/337,177, filed on Dec. 17, 2008, now Pat. No. 8,013,992.

(51) Int. Cl.
*G01J 3/44* (2006.01)
(52) U.S. Cl.
USPC .......................................... 356/301
(58) Field of Classification Search
USPC .............................. 356/72–73, 301
See application file for complete search history.

(56) References Cited

U.S. PATENT DOCUMENTS

| | | | |
|---|---|---|---|
| 7,057,565 B1 | 6/2006 | Liu | |
| 7,205,940 B2 | 4/2007 | Anazawa et al. | |
| 7,450,227 B2 * | 11/2008 | Dwight et al. | 356/301 |
| 7,733,481 B1 | 6/2010 | Bratkovski et al. | |
| 2005/0249901 A1 * | 11/2005 | Yializis et al. | 428/35.7 |
| 2006/0045988 A1 | 3/2006 | Guo et al. | |
| 2010/0140564 A1 | 6/2010 | Overbreek et al. | |

OTHER PUBLICATIONS

Biswas, A., et al., Large broadband visible to infrared plasmonic absorption from Ag nanoparticles with a fractal structure embedded in a Teflon AF® matrix. Appl. Phys. Lett., 2006. 88: 013103, p. 1-3.
Biswas, A. et al., Networks of ultra-fine Ag nanocrystals in a Teflon AF® matrix by vapour phase e-beam-assisted deposition. Nanotechnology, 2007. 18: 305602, p. 1-6.
A. Biswas et al.,"Controlled Generation of Ni Nanoparticles in the Capping Layers of Teflon AF by Vapor-Phase Tandem Evaporation," Nano Letters, 2003, 3 (1), pp. 69-73.
Biswas, A. et al., "Nanocomposites of Vapour Phase Deposited Teflon AF Containing Ni Clusters", Solid State Phenom., 2003: 94, 285.
T. Hasell et al., Sliver Nanoparticle Impregnated Polycarbonate Substrates for Surface Enhanced Raman Spectroscopy, Advanced Functional Material, 2008, 18, 1265-1271.

* cited by examiner

*Primary Examiner* — Tarifur Chowdhury
*Assistant Examiner* — Abdullahi Nur
(74) *Attorney, Agent, or Firm* — Morris, Manning & Martin, LLP; Tim Tingkang Xia, Esq.

(57) ABSTRACT

A method of fabricating a surface enhanced Raman scattering (SERS) substrate. In one embodiment, the method has the steps of simultaneously evaporating a metal at a first evaporation rate and a polymer at a second evaporation rate different from the first evaporation rate, to form a nanocomposite of the metal and the polymer, depositing the nanocomposite onto a substrate, and applying an etching process to the deposited nanocomposite on the substrate to remove the polymer material, thereby forming an SERS substrate.

12 Claims, 9 Drawing Sheets

METHODS OF FABRICATING SURFACE ENHANCED RAMAN SCATTERING SUBSTRATES

CROSS-REFERENCE TO RELATED PATENT APPLICATION

This application is a Continuation patent application of U.S. patent application Ser. No. 12/337,177, filed Dec. 17, 2008 now U.S. Pat. No. 8,013,992, entitled "METHODS OF FABRICATING SURFACE ENHANCED RAMAN SCATTERING SUBSTRATES", by Alexandru S. Biris et al., which status is allowed, and the disclosure of which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [4] represents the 4$^{th}$ reference cited in the reference list, namely, Biswas, A. et al., Solid State Phenom., 2003: 94, 285.

FIELD OF THE INVENTION

The present invention generally relates to surface enhanced Raman scattering (SERS), and more particularly, to methods of fabricating an SERS substrate and applications of the same.

BACKGROUND OF THE INVENTION

Surface enhanced Raman Scattering is a surface sensitive technique relating to a phenomenon that occurs when molecules are adsorbed onto suitably rough surfaces of noble metal having appropriate nanomorphologies. Noble metal nanostructures with uniform surface roughness are considered of high importance for the preparation of stable SERS substrates with high enhancement factors. In addition, other nanostructural features such as shape and homogeneous distribution of the metal nano-features throughout the substrate surface can be considered important requirements in the design of more analytically-sensitive and reliable SERS substrates. In this context, some approaches including self-assembled metal colloid monolayers and fractal-like colloidal aggregates of Ag nanoparticles possessing appropriate surface roughness have been conducted. Unfortunately, aggregates of the metal colloids tend to agglomerate, resulting in poor reproducibility of the SERS signals. This creates a major obstacle in the preparation of stable SERS substrates. While approaches based on templating or electron beam lithography techniques may be useful to generate specific metal nanostructures with desired morphologies, they require quite complex preparation methods and are not suitable for preparing efficient large-scale SERS substrates.

Regarding fabrication and development of these nanocomposites, it is desirable to restrict the nanoparticles to a small size regime (<100 nm) while maintaining a highly uniform dispersion of the nanocrystals, in order to exploit the unique properties of the metal nanocrystal networks. However, it is a conflicting process to simultaneously control the nanoparticle size while increasing the nanoparticle volume filling in the polymer matrix (i.e. packing density) due to the strong tendency of nanoparticles to agglomerate and form larger sized islands. A straightforward implementation of polymer-metal fractal nanocomposites for highly active SERS substrates for such applications has not yet been demonstrated.

Therefore, a heretofore unaddressed need exists in the art to address the aforementioned deficiencies and inadequacies.

SUMMARY OF THE INVENTION

The problems of agglomeration of metal nanoparticle aggregates can largely be overcome by designing and engineering suitable nanocomposites having metal nanoparticles embedded in various polymer frames. Over the last few years, a new class of nanocomposite materials has been developed for their unusual optical properties, including enhancements of the internal electrical field leading to large nonlinear effects. This class of materials consists of interpenetrating networks of metallic nanoparticles with a range of shapes and sizes embedded in dielectric matrices, such as polymers. Such networks of nanoparticles exhibit a fractal structure which forms at a certain composition just below the metal percolation threshold, where the neighboring nanoparticles are still quite densely packed but separated by narrow polymer gaps, the so-called quantum contacts.

These fractal nanocomposites with unique nanostructural features that are formed at just below the percolation threshold possess fascinating electromagnetic and optical properties. The localization of surface plasmons (electromagnetic wave induced coherent charge density oscillations) in such fractal nanocomposites can lead to strongly enhanced electric fields due to electromagnetic field confinement within the surface of the metallic nanoparticles and the narrow interparticle gaps, the so called "hot spots". This field enhancement can take place within a broad spectral range, including the visible and infrared parts of the spectrum. Theory predicts a dramatic enhancement in the SERS signals occurring at just below the percolation threshold due to the electromagnetic energy localization in hot spots that are generated in large numbers in such nanocomposites. This energy localization decreases as the metal volume filling reaches a value above the percolation threshold and the features of quantum contacts between the nanoparticles are significantly diminished. This process results in the propagation of localized plasmons and the SERS intensity drops sharply. Therefore, controlled creation of nanometric electromagnetic field confinement in metal-polymer heterostructures for realizing high SERS is of great interest. In addition, appropriate roughness on the critical nanoscale (<100 nm) which is highly desired for SERS enhancements can be achieved from such networks of metallic nanoparticles present in the fractal nanocomposites by potentially removing the polymer matrix by chemical or physical processes. These metal nanostructural features can be exploited to prepare well-defined, stable substrates with very high enhancement factors in a wide spectral range suitable for a variety of applications ranging from biological detection to medicine, electronics, environmental science and chemistry.

In one aspect, the present invention relates to a method of fabricating a surface enhanced Raman scattering (SERS) substrate. In one embodiment, the method includes the steps of simultaneously evaporating a metal at a first evaporation rate and a polymer at a second evaporation rate different from the first evaporation rate, to form a nanocomposite of the metal and the polymer, depositing the nanocomposite onto a substrate, and applying an etching process to remove the polymer material. In another embodiment, an SERS substrate is fabricated according to this method.

In one embodiment, the step of simultaneously evaporating the metal at a first evaporation rate and the polymer at a second evaporation rate further includes the steps of adjusting the first evaporation rate relative to the second evaporation rate for producing a predetermined concentration of the metal in the resulting nanocomposite. The predetermined concentration of the metal has nanoparticles of the metal embedded within a nanoscale matrix of the polymer. Also, the nanoparticles of the metal have a diameter of less than 100 nanometers and are uniformly dispersed throughout the matrix of the second material, the nanocomposite has a morphology corresponding to just below the percolation threshold, the inter-particle separation distance between nanoparticles of the first material is about 1 nanometer, and the nanocomposite has an fcc crystalline structure.

In another aspect, the present invention relates to a method of fabricating a surface enhanced Raman spectroscopy (SERS) substrate. In one embodiment, the method includes simultaneously evaporating a first material at a first evaporation rate and a second material at a second evaporation rate that is different from the first evaporation rate, to form a composite of the first material and the second material, depositing the composite onto a substrate, and removing the second material from the deposited composite on the substrate. In another embodiment, an SERS substrate is fabricated according to this method.

In one embodiment, the first material is a metal and the second material is a polymer. More specifically, the first material is silver and the second material is a polymer matrix. Also, the step of simultaneously evaporating the first material at the first evaporation rate and the second material at a second evaporation rate has the step of adjusting the first evaporation rate relative to the second evaporation rate so as to a predetermined concentration of the first material in the composite. The predetermined concentration of the first material in the composite has particles of the first material embedded within a matrix of the second material, where the composite has predetermined dimensions, inter-particle separation, and crystalline structure.

In one embodiment, the steps of simultaneously evaporating the first material and the second material to form the composite and the step of depositing the composite onto a substrate further have the step of delivering an electron beam so as to generate vapor-phase codeposition of the first material and the second material without causing deterioration of the second material. The composite is a nanocomposite and the particles of the first material are nanoparticles having a diameter of less than 100 nanometers, uniformly dispersed throughout the matrix of the second material. The composite has a fractal structure with a morphology corresponding to below the percolation threshold, the inter-particle separation distance between particles of the first material is in a range of about 0.5 to 1.2 nanometers, and the composite has an fcc crystalline structure. In another embodiment, the step of removing the second material further includes the steps of sputtering at least one film of the first material, on one side of the composite, and exposing the entire composite to a plasma etching treatment for a predetermined time for removing the matrix of the second material while retaining the structures of the first material. In this embodiment, the predetermined time is about 2 minutes.

In yet another aspect, the present invention relates to a method of fabricating a surface enhanced Raman spectroscopy (SERS) substrate. In one embodiment, the method includes the step of forming a fractal metal-polymer nanocomposite of at least one metal and at least one polymer, having a metal loading for forming a morphology corresponding to below the percolation threshold. In this embodiment, the step of forming the fractal metal-polymer nanocomposite further has the step of performing vapor-phase codeposition of the at least one metal and at least one polymer. In another embodiment, an SERS substrate is fabricated according to this method.

In one embodiment, the vapor-phase codeposition step can be performed by delivering a beam of electrons so as to simultaneously evaporate the at least one metal and the at least one polymer to form the fractal metal-polymer nanocomposite, where the nanocomposite has nanoparticles of the at least one metal embedded within a matrix of the polymer. In this embodiment, the fractal metal-polymer nanocomposite includes networks of individually assembled metal nanocrystals held together within the polymer matrix such as to form irregularly shaped clusters, where the nanocomposite has predetermined dimensions, inter-particle separation, and crystalline structure. The inter-particle distance between metal nanoparticles in the nanocomposite is in a range of about 0.5 to 1.2 nanometers. The at least one metal includes silver and the at least one polymer includes Teflon AF®. Also in this embodiment, each cluster includes about 6 nanocrystals and the diameter of each cluster is less than 100 nanometers.

In yet another aspect, the present invention relates to a method of identifying a chemical or biological sample, including the steps of fabricating a surface enhanced Raman spectroscopy substrate formed of a fractal metal-polymer nanocomposite having morphology corresponding to below the percolation threshold, placing a solution containing the chemical or biological sample on the SERS substrate, performing a Raman analysis on the sample, and comparing the Raman signal generated from the sample on the SERS substrate with a signal from a control solution so as to identify the sample. In one embodiment, the metal in the fractal metal-polymer nanocomposite is silver and the polymer in the fractal metal-polymer nanocomposite is Teflon AF®. Also, the inter-particle separation distance of the metal nanoparticles is about 1 nanometer, and the sample includes double-stranded deoxyribonucleic acid.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1A:
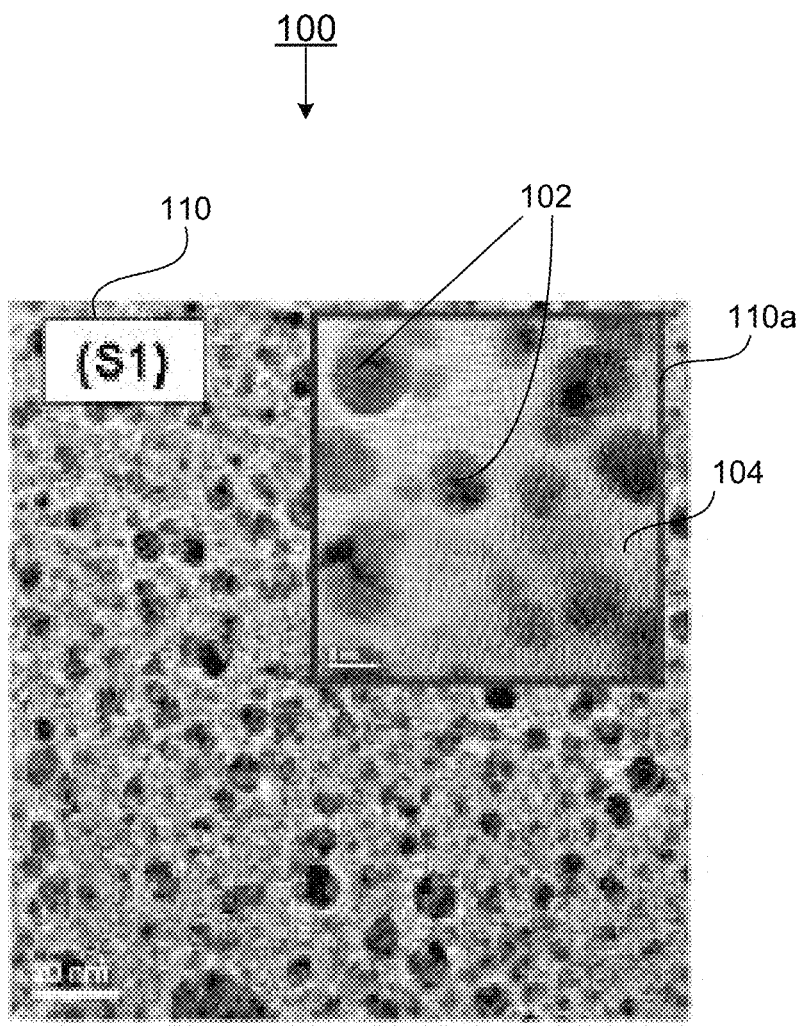
FIG. 1 shows transmission electron micrographs along with higher magnified images and the selected area electron diffraction (SAED) patterns (inset pictures) of Teflon AF/Ag nanocomposites according to one embodiment of the present invention: (A) S1 below percolation threshold morphology with widely separated Ag nanoparticles; (B) S2 just below the percolation threshold morphology; and (C) S3 just above the percolation threshold morphology.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

As used herein, "percolation threshold" refers to a composition of a material at which the material becomes highly conductive [2]. A common percolation model is to take a regular lattice, like a square lattice, and make it into a random network by randomly "occupying" sites (vertices) or bonds (edges) with a statistically independent probability p. At a critical threshold, $p_c$, long-range connectivity first appears, and this is called the percolation threshold.

As used herein, the term "Raman spectroscopy" refers to an optical technique that probes the specific molecular content of a sample by collecting in-elastically scattered light. As photons propagate through a medium, they undergo both absorptive and scattering events. In absorption, the energy of the photons is completely transferred to the material, allowing either heat transfer (internal conversion) or re-emission phenomena such as fluorescence and phosphorescence to occur. Scattering, however, is normally an in-elastic process, in which the incident photons retain their energy. In Raman scattering, the photons either donate or acquire energy from the medium, on a molecular level. The energy transfers associated with Raman scattering are on the order of the vibrational modes of the molecule. These vibrational modes are molecularly specific, giving every molecule a unique Raman spectral signature.

As used herein, "SERS" is an abbreviation for surface enhanced Raman scattering, a surface sensitive technique that results in the enhancement of Raman scattering by molecules adsorbed on rough metal surfaces [1].

As used herein, "XRD" is an abbreviation for X-ray diffraction. X-ray diffraction techniques are a family of non-destructive analytical techniques which reveal information about the crystallographic structure, chemical composition, and physical properties of materials and thin films. These techniques are based on observing the scattered intensity of an X-ray beam hitting a sample as a function of incident and scattered angle, polarization, and wavelength or energy.

Overview of the Invention

The description will be made as to the embodiments of the present invention in conjunction with the accompanying drawings. In accordance with the purposes of this invention, as embodied and broadly described herein, this invention, in one aspect, relates to a method of fabricating a surface enhanced Raman scattering (SERS) substrate.

Figure 4:
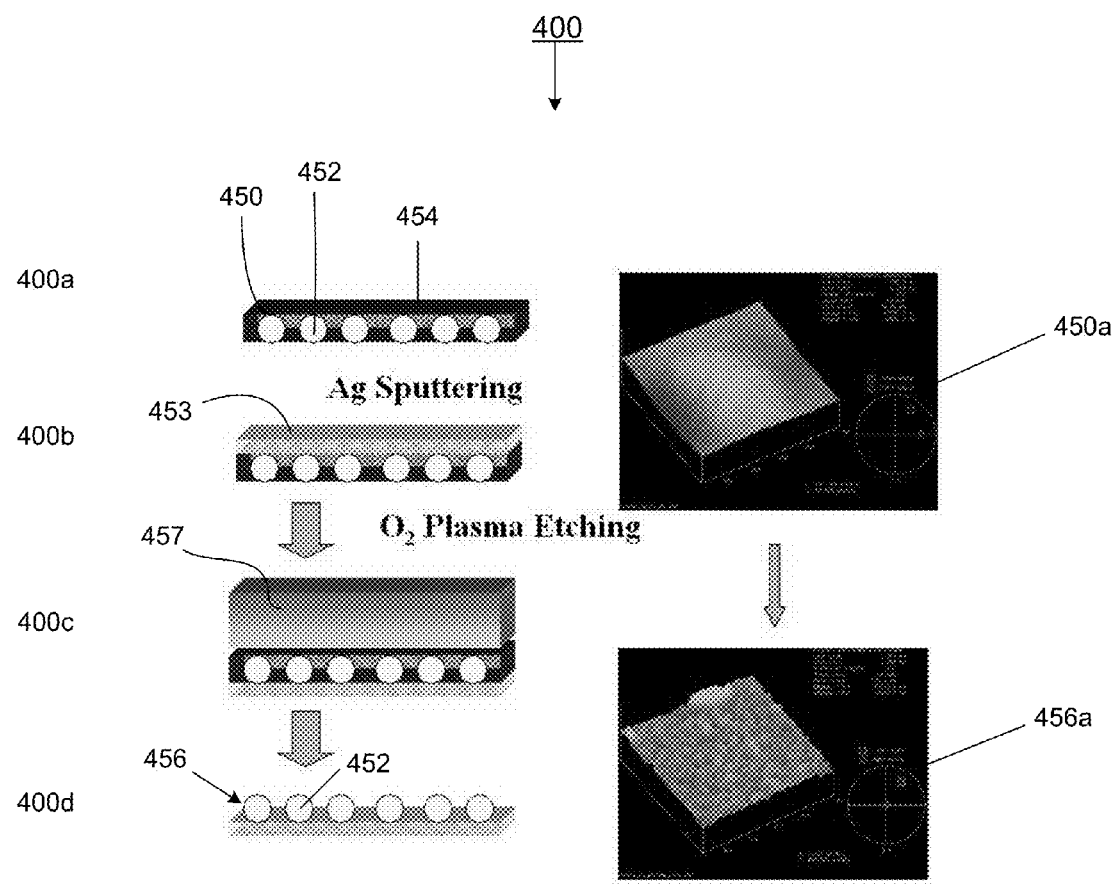
FIG. 4 shows the process used for the formation of highly active SERS substrates starting from the Ag/Teflon AF® nanocomposite films; the polymer was etched away by a highly reactive $O_2$ plasma process (20 W, 2 minutes).

Now referring to FIGS. 1 and 4, in one embodiment, the method includes the steps of simultaneously evaporating a metal 122 at a first evaporation rate and a polymer 124 at a second evaporation rate different from the first evaporation rate, to form a nanocomposite 120 of the metal 122 and the polymer 124, depositing the nanocomposite 120 onto a substrate, and, applying an etching process 400a, 400b, 400c, 400d to remove the polymer material 454. The step of simultaneously evaporating the metal 122 at a first evaporation rate and the polymer 124 at a second evaporation rate includes the step of adjusting the first evaporation rate relative to the second evaporation rate for producing a predetermined concentration of the metal 122 in the resulting nanocomposite 120. The predetermined concentration of the metal 122 comprises nanoparticles of the metal 122 embedded within a nanoscale matrix of the polymer 124. With regard to the nanoparticles of the metal, they have a diameter of less than 100 nanometers and are uniformly dispersed throughout the matrix of the second material 124. Also, the nanocomposite 120 has a morphology corresponding to just below the percolation threshold, the inter-particle separation distance between nanoparticles of the first material 122 is about 1 nanometer, and the nanocomposite 120 has an fcc crystalline structure. In one embodiment (see e.g. S2, FIG. 1), the first material is a metal, and particularly silver, and the polymer is a polymer matrix including Teflon AFC®. The steps of simultaneously evaporating the first material 122 and the second material 124 to form the composite and the step of depositing the composite 120 onto a substrate further include the step of delivering an electron beam so as to generate vapor-phase codeposition of the first material 122 and the second material 124 without causing decomposition of the second material 124. The step of removing the second material 124 further includes the steps of sputtering 400a, 400b at least one film 453 of the first material 452, on one side of the composite 452, 454, and, exposing (400c, 400d) the entire composite 452, 454 to a plasma etching treatment 457 for a predetermined time, for removing the matrix of the second material 454 while retaining the structures of the first material 452. In one embodiment, the predetermined time is about 2 minutes.

In another aspect, the present invention relates to a method of identifying a chemical or biological sample, comprising the steps of fabricating a surface enhanced Raman spectroscopy substrate formed of a fractal metal-polymer nanocomposite 120 having morphology corresponding to below the percolation threshold, placing a solution containing the chemical or biological sample on the SERS substrate, performing a Raman analysis on the sample, and, comparing the Raman signal generated from the sample on the SERS substrate with a signal from a control solution so as to identify the sample. In one embodiment, the sample comprises double-stranded deoxyribonucleic acid.

These and other aspects of the present invention are more specifically described below.

IMPLEMENTATIONS AND EXAMPLES OF THE INVENTION

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

An approach based on tailored polymer-metal fractal nanocomposites for the fabrication of highly active SERS substrates is disclosed. The nanocomposites were fabricated by a versatile single step method electron-beam (e-beam)-assisted codeposition of polymers and metals [3],[4] that allows simultaneous control of the metal nanoparticle sizes and provided an uniform dispersion while increasing the nanoparticle volume filling in the polymer matrix in order to reach the percolation threshold. The e-beam-assisted vapor-phase codeposition fabrication process is relatively straight forward compared to other more complex multi-step chemical synthesis routes or lithography previously used to synthesize colloidal aggregates of Ag and Au nanoparticles. The method is essentially an e-beam-assisted effusion cell process. A metal (molybdenum, tantalum or tungsten) crucible [2] that is bombarded with electrons is used as an effusion cell to evaporate the polymer without decomposing it. The e-beam source can heat the target material to temperatures in excess of 3000° C. The composites were deposited on glass substrates. Simultaneous evaporation of the two components produced highly uniform 3 dimensionally distributed Ag nanoparticles in the polymer matrix. The relative evaporation rates of polymer and metal were adjusted to fabricate nanocomposites with different metal concentrations from a very dilute structure (widely separated nanoparticles) to denser nanoparticle assemblies (below and above the percolation threshold). They are able to provide significant SERS enhancement, which as expected was found to be highly dependent upon interparticle distance.

A plasma etching process is applied to remove the polymer structures that allowed the formation of Ag structures with very uniform and controllable interparticle gaps that were proved to provide significant SERS enhancement. Finally, to prepare SERS substrates of nanocomposites with just below the percolation threshold morphology, a plasma etching process is applied to remove the polymer structures of the nanocomposites while retaining the metal nanostructures. The efficiency of such ultra-sensitive SERS substrates for direct detection of a typical biological sample such as double-stranded deoxyribonucleic acid (dsDNA), is demonstrated. The employed method of one or more of the examples can be leveraged to develop large-scale, highly active SERS substrates for spectroscopic-based advanced sensors for rapid, quantitative detection and analysis of various biological and chemical materials.

EXAMPLE 1

Nanocomposite morphology such as Ag nanoparticle dimensions, inter-particle separation, and crystal structure were investigated by TEM using a Philips CM200 operated at 200 kV. The Raman scattering spectra were recorded at room temperature with a High Resolution LabRam system (Horiba HR 800 UV Spectrometer) equipped with 1800 and 600 grooves/mm holographic gratings. The laser excitation of 632.8 nm output of a He—Ne laser was used for the analysis of the samples and the signal was collected in the backscattering geometry with the help of a confocal Raman microscope (high stability BX41) equipped with Olympus objectives (100×, 50×, 10×). The laser spot diameter is about 1 µm. A Peltier CCD camera detection system was employed for the data acquisition. The spectral resolution is 1 cm$^{-1}$ and the collected signal is generally averaged over 10 spots. The X-Ray Diffraction measurements were performed on a Bruker D8 Discovery diffractometer, capable of analyzing very small sample quantities, inhomogeneous or oriented samples of complex shape geometry. The diffractometer is equipped with the 2 D General Area Detector Diffraction System (GADDS) for fast data acquisition. The D8 DISCOVER diffractometer with GADDS illuminates samples with a tuned monochromatic and parallel x-ray beam and the spatially diffracted x-rays are then measured and evaluated using software from Bruker's GADDSPLUS suite. Peak to background of the data is close to the theoretical limit(s) because of the unique sensitivity of the HI-STAR detector. Surface morphology studies were performed by using a SPI Dimension 3100 Atomic Force Microscope that utilizes standard and advanced SPM imaging modes to measure surface characteristics. Plasma treatment was carried out using MCS Plasma System model HF-3. Oxygen was used as the processing gas and the operating pressure was 150 mtorr. The plasma reactor consisted of two parallel aluminum electrodes and the plasma was generated between the electrodes using a 13.56 MHz RF power supply with an impedance matching network. Samples were treated for 2 minutes with applied plasma power of 20 W. The reactor has a unique gas flow design in which gas is dispersed into the chamber using a series of inlets from the top electrode.

FIG. 1 shows TEM results of fabricated nanocomposites with various Ag volume fillings (S1, S2, S3). S1 shows widely separated Ag nanoparticles dispersed in the Teflon AF® matrix. The analysis of the micrograph shows the average particle size of about 9 nm with the polymer separation between the particles of about 10 nm (Sample S1). S2 shows a micrograph of typical morphology of just-below percolation threshold features and the SAED patterns (shown in the inset) indicate an fcc crystalline structure of the Ag nanostructures. The uniform surface roughness generated by the closely packed Ag nanocrystals is evidenced from the TEM micrograph. The small individual Ag nanocrystals, their specific network arrangement and their close contact are the key morphological features of this nanocomposite. They can be described as networks of individually assembled silver nanoparticles/nanocrystals held together within the polymer matrix forming irregularly shaped clusters. The smallest Ag cluster (about 100 nm in diameter) was found to be composed of approximately 6 Ag nanocrystals. TEM analysis showed average Ag nanoparticles/nanocrystal size of about 20 nm along with the separation of Ag nanoparticles in the clusters by about 0.8 nm (FIG. 1, Sample S2). With a uniform dispersion of the nanoparticles, extremely high density of such tiny interparticle contacts is generated throughout the polymer matrix.

Figure 1B:
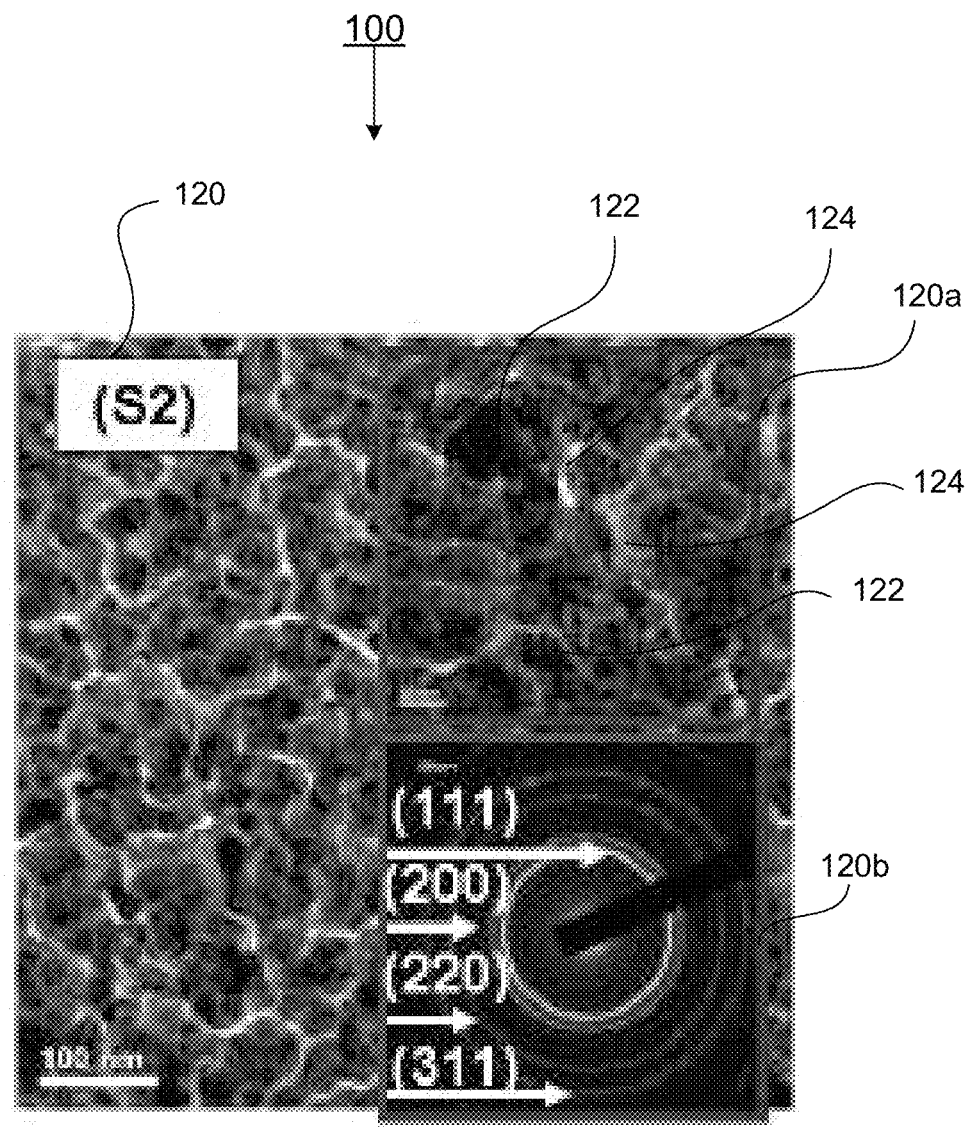
Figure 1C:
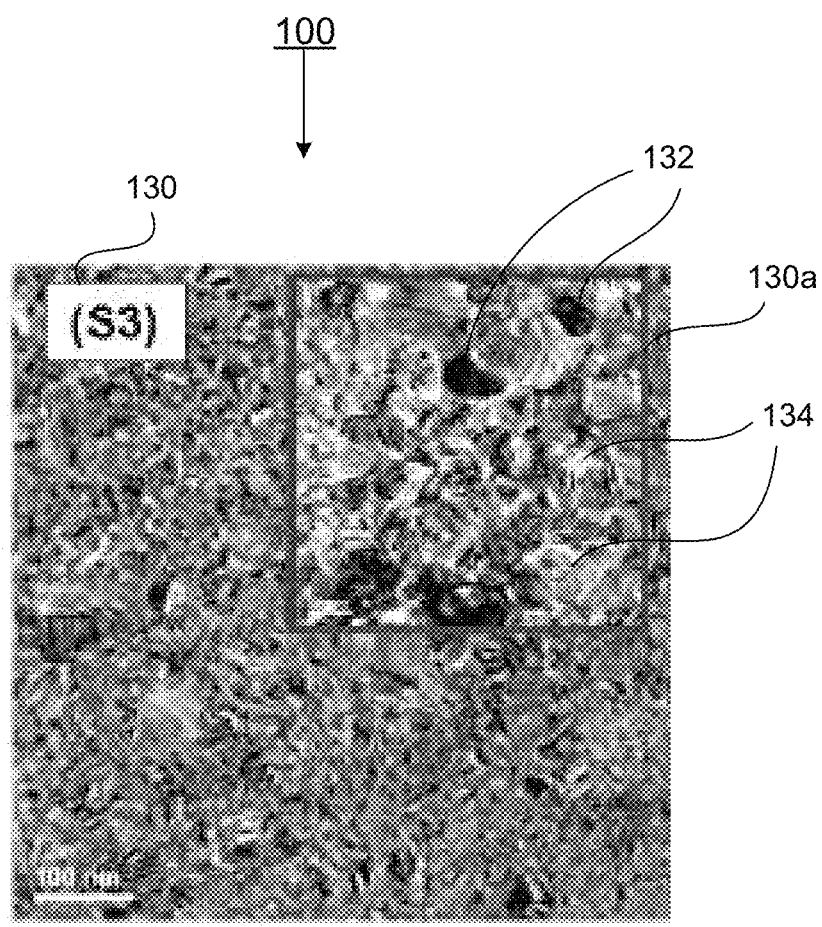

As shown in detail in FIG. 1, transmission electron micrographs 110, 120, 130 (S1, S2, S3) along with higher magnified images 110a, 120a, 130a and the selected area electron diffraction (SAED) patterns (inset pictures) of Teflon AF/Ag nanocomposites are disclosed, respectively. In particular, FIG. 1A (S1) shows below percolation threshold morphology with widely separated Ag nanoparticles 102. FIG. 1B (S2) shows just below the percolation threshold morphology. FIG. 1C (S3) shows just above the percolation threshold morphology. FIG. 1C (S3) shows that the Ag nanoparticles 132 are fused together forming larger Ag crystallites at higher metal volume filling. This microstructure can be attributed to the coalescence and growth of the nanoparticles 132 at a metal coverage that exceeds the percolation threshold. The degree of surface roughness is lowered as compared to the just-below percolation threshold sample (FIG. 1B (S2)) due to the smoothening of the Ag nanoparticles bumps as a result of coalescence of nanoparticles into larger nanocrystals/nanoparticles. The average Ag crystallite size is observed to be about 58 nm with the polymer separation between the clusters of about 2.3 nm (FIG. 1C, sample 130 (S3)).

Figure 2:
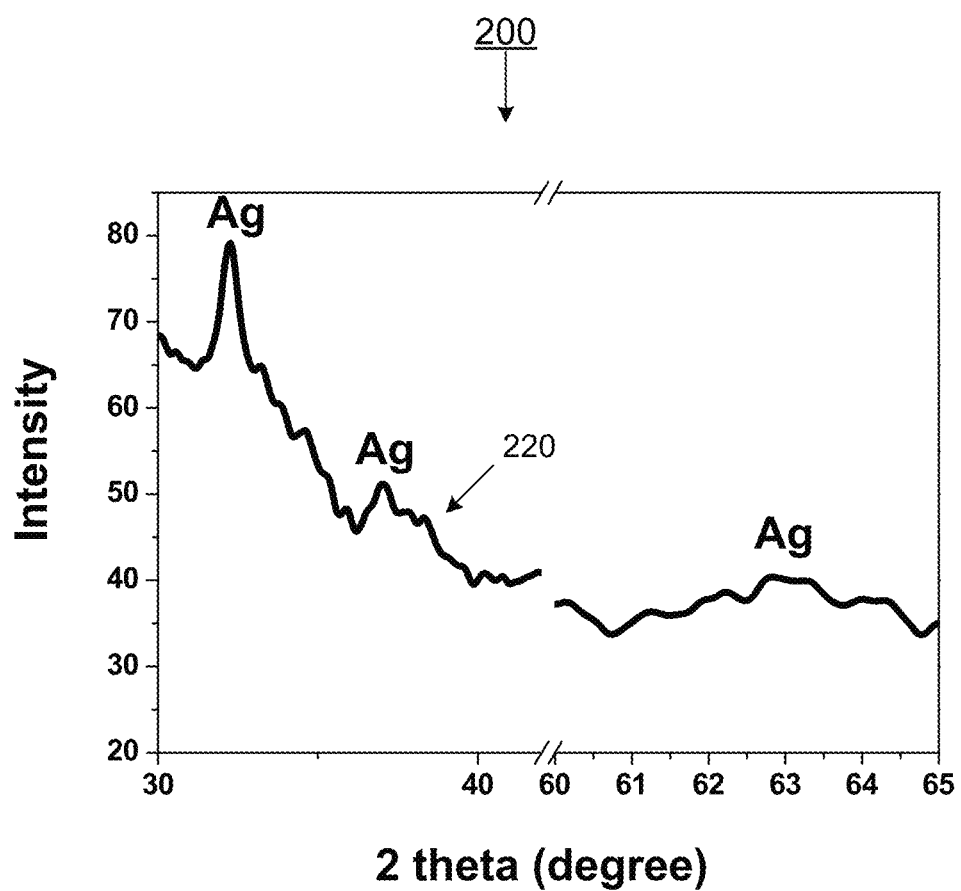
FIG. 2 shows XRD data for the S2 sample that indicates the presence of fcc Ag in the polymer matrix, according to one embodiment of the present invention.
Figure 3A:
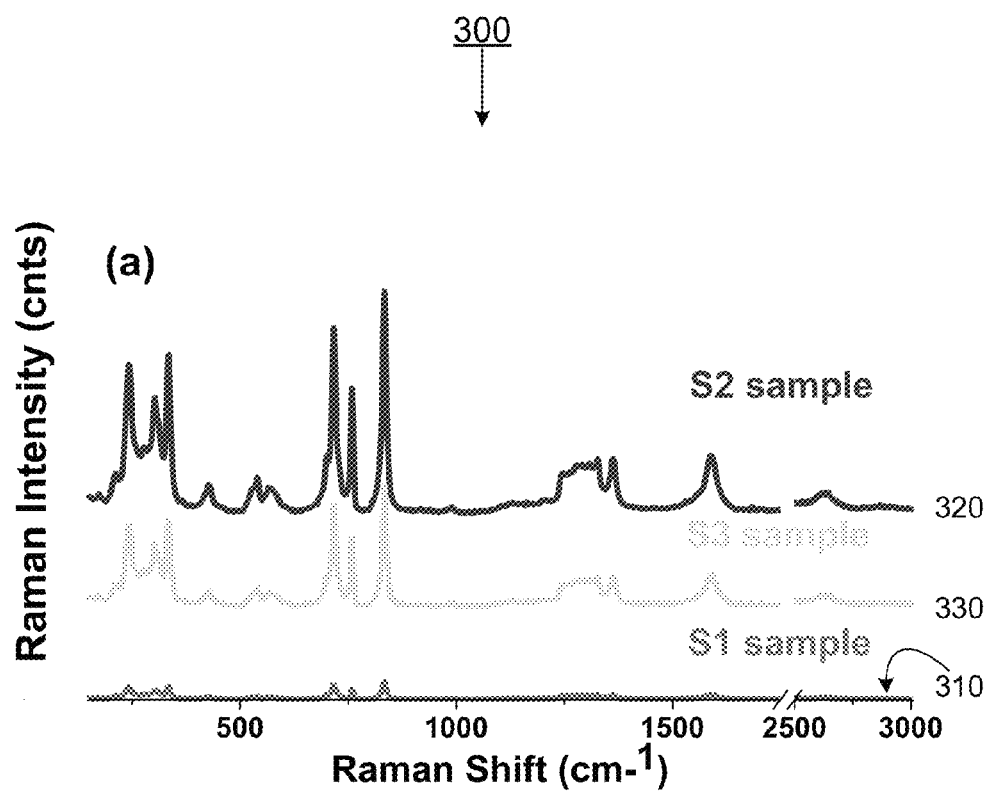
FIG. 3 shows (A) the Raman spectra obtained from the S1, S2, and S3 composites and (B) the SERS signal intensity of the 733 cm-1 peak of as a function of the Ag inter-particulate distance, along with a second order exponential fitting, according to one embodiment of the present invention.

FIG. 2 shows the X-Ray Diffraction peaks of the S2 sample 120, indicating the presence of Ag in metallic state (with a crystalline spacegroup Fm-3m(225), a=4.085, d=2.3587, 2.043, 1.444, 1.232, 1.179). The XRD data of the S2 sample indicates the presence of fcc Ag in the polymer matrix. The Ag/Teflon AF® films were analyzed by Raman spectroscopy (633 nm excitation, 20 mW, acquisition time 5 sec) and FIG. 3a shows corresponding scattering data of the samples 310, 320, and 330 (S1, S2 and S3, respectively). These discoveries indicate that the SERS enhancement is strongly dependent upon the interparticle gap and the nanocomposites structural morphology. It shows a very high SERS enhancement from the nanocomposites with the just-below percolation threshold morphology (sample S2) with the narrowest polymer gap of about 0.8 nm (FIG. 1B). As shown, as the inter-particle distance increased, the intensity of the Raman peaks decreased significantly. Several peaks are present from 100 to 2000 $cm^{-1}$ in the PTFE-based polymer Raman spectra, but the most intense peak is the one present at 733 $cm^{-1}$, which corresponds to the $A_1$ stretching mode of $CF_4$.

Figure 3B:
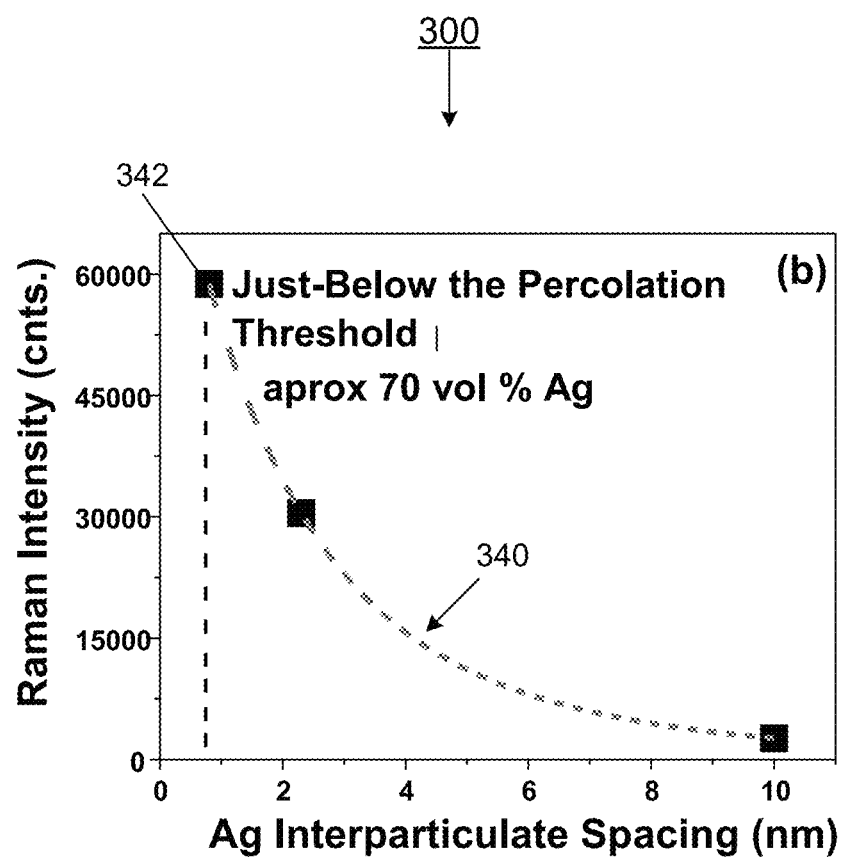

FIG. 3 shows in detail (a) The Raman spectra obtained from the S1, S2, S3 (310, 320, 330) composites, and (b) the SERS signal intensity of the 733 $cm^{-1}$ peak of as a function of the Ag inter-particulate distance along with a second order exponential fitting. Analyzing the intensity of the 733 $cm^{-1}$ peak as collected from the Raman spectra of the S1, S2, S3 (310, 320, 330) samples a non-linear relationship (see 340) between the Raman enhancement, and the distance between the Ag surfaces can be determined as shown in FIG. 3b. In order to understand the remarkable SERS enhancement from sample 320 (corresponding to 342 in FIG. 3b), it is needed to consider the possible light localization in the so called hotspots on roughened surfaces of Ag nanoparticles where random, extremely tiny nanojunctions between surface protrusions form cavity-like structures for field enhancement. A recent theoretical model suggested that such plasmonic cavities with nanometric dielectric gaps could indeed confine electromagnetic energy into both physical and effective mode volumes far below the diffraction limit. Such a design of metal nanoscale cavities has been considered very important for single molecule SERS. Further, in another theoretical report, it was found that electric field confinement and the enhancement rapidly varies with the inter particle gaps and very large SERS can be obtained only for interparticle gaps of the order of 1 nm or less. In the present case, very high density tiny contacts between Ag nanoparticles (about 0.8 nm) can lead to the formation of large number of hot spots where the confinement and the storage of the electromagnetic energy is possible. This can result in the dramatic enhancement of the SERS signal as shown in (FIG. 3b). For the case of just above the percolation threshold S3 (330) with the inter particle gap of about 2.3 nm, a sharp decrease in the SERS signal is observed. This may be attributed to the propagation of localized plasmons that causes a greatly reduced number of hot spots and subsequently the energy localization is destroyed.

Figure 5:
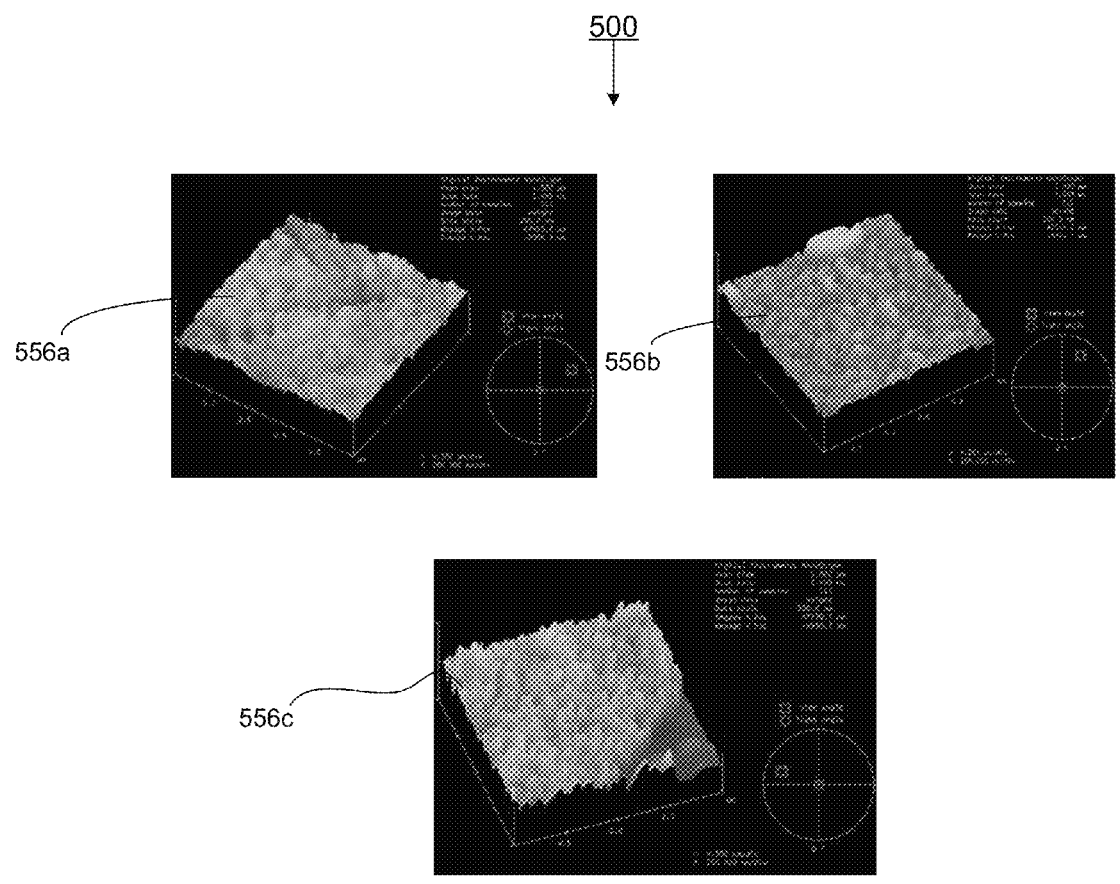
FIG. 5 shows AFM analysis of the S2 (556a), S3 (556b) and S1 (556c) samples after exposure to $O_2$ plasma (20 W) for 2 minutes, according to one embodiment of the present invention; variation of the inter-particle distance can be observed, which has a strong correlation with the TEM data.

To prove the strong Raman enhancement properties of the Sample S2, referring now to FIG. 4, the films were further prepared as follows: (1) Ag films were sputtered on one side (step 400a), and (2) the entire films were exposed to an $O_2$ plasma etching (20 W) (step 400b) in order to remove the polymer matrix (steps 400c and 400d). In general, about 2 minutes of treatment were found enough for the complete polymer removal and the formation of very uniform Ag structured onto the Ag sputtered films (see 456a). FIG. 5 shows the AFM images 556a, 556b, and 556c of the three samples after the plasma etching treatment, which clearly indicates a gradually increased distance between the Ag nanoparticles. In detail, FIG. 4 shows the process used for the formation of highly active SERS substrates starting from the Ag/Teflon AF® nanocomposite films (450a). The polymer is etched away (step 400c) by a highly reactive $O_2$ plasma process (20 W, 2 minutes). FIG. 5 shows AFM analysis of the S2 (a), S3 (b), and S1 (c) samples after the exposure to $O_2$ plasma (20 W) for 2 minutes. The variation of the inter-particle distance can be observed which has a strong correlation with the TEM data.

EXAMPLE 2

The Ag structures formed, as described above in connection with Example 1, were also proved to provide significant SERS enhancement of typical biological systems such as double-stranded deoxyribonucleic acid (dsDNA). These advanced nanocomposite films could be used for the development of large-scale spectroscopic-based sensors for direct detection and analysis of various biological and chemical samples.

Figure 6:
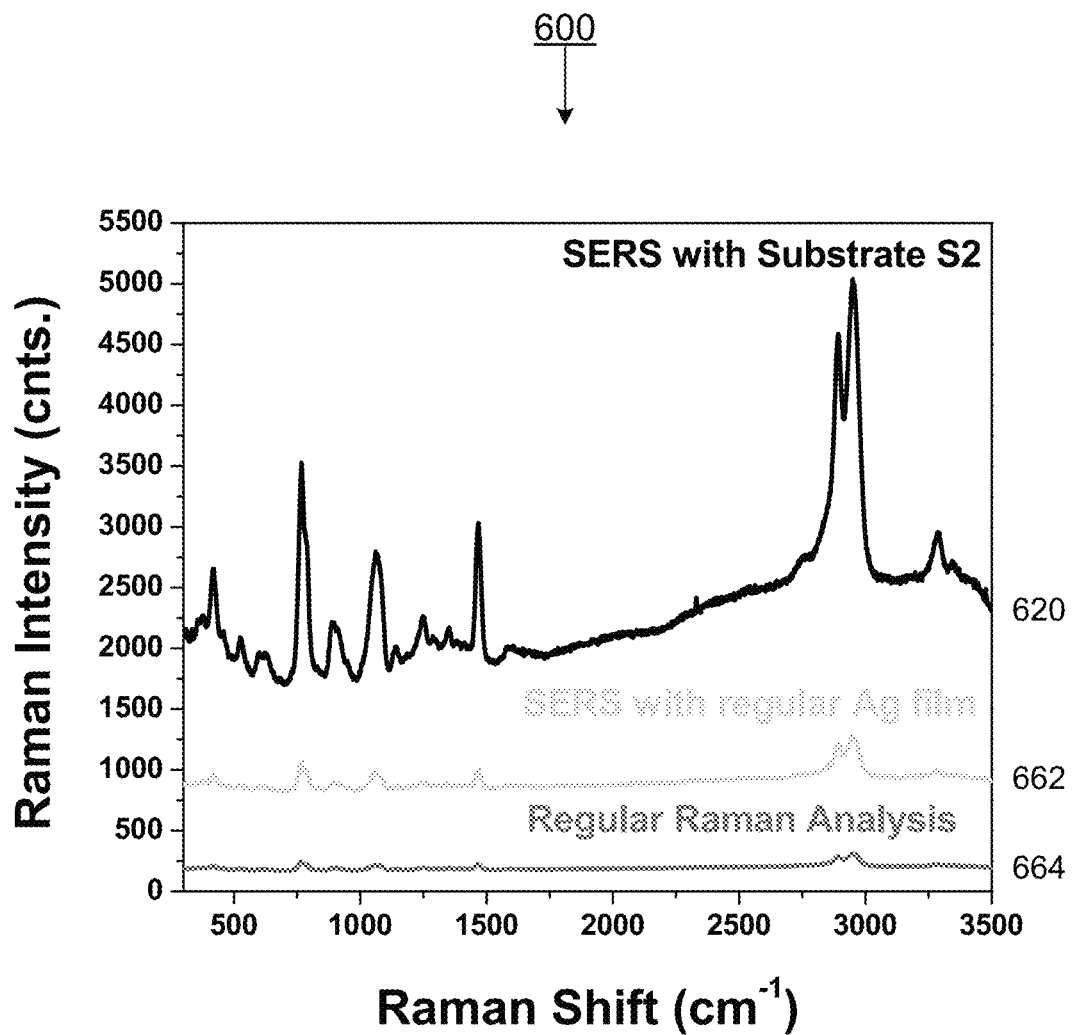
FIG. 6 shows a comparison of the Raman signal of a dsDNA (Sigma Aldrich) dispersed in a buffer solution that was acquired in identical conditions (633 nm laser excitation, 20 mW, 2 sec. acquisition time) by regular Raman, from sputtered Ag film and from the sample S2, as shown in FIG. 5, according to one embodiment of the present invention.

To further understand the SERS properties of these advanced functional films, a drop of a DNA/water solution was placed on top of the S2 sample after plasma treatment, and on an Ag film sputtered onto the top surface of a glass slide. Double-stranded deoxyribonucleic acid (dsDNA) was obtained from Sigma-Aldrich. 5 mL of dsDNA (0.2 mg/mL) was added to a buffer solution (10 mM, pH=7.3) and used for the Raman studies. The results are presented in FIG. 6 as a comparison to the Raman data of the solution without any Ag supported enhancement (664). The data clearly indicate the extremely large enhancement provided by the S2 films (620) compared with the other two situations (662, 664). Furthermore, these results show the potential of this system for a convenient and powerful SERS-active substrate for biological sample detection and analysis, and the results also indicate that the development of Ag-polymer nanocomposites with the metal loading slightly below the percolation threshold could produce extremely significant SERS signal. This can be further used for the development of various spectroscopic-based sensors. In detail, FIG. 6 shows a comparison of the Raman signal 620 of a dsDNA (Sigma Aldrich) dispersed in a buffer solution that was acquired in identical conditions (633 nm laser excitation, 20 mW, 2 sec. acquisition time) by regular Raman, from sputtered Ag film 662 and from the sample S2 (620), as also shown in FIG. 5.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1] Biswas, A., et al., *Large broadband visible to infrared plasmonic absorption from Ag nanoparticles with a fractal structure embedded in a Teflon AR® matrix*. Appl. Phys. Lett., 2006. 88: 013103, p. 1-3.

[2] Biswas, A. et al., *Networks of ultra-fine Ag nanocrystals in a Teflon AR® matrix by vapour phase e-beam-assisted deposition*. Nanotechnology, 2007. 18: 305602, p. 1-6.

[3] Biswas, A. et al., Nano Lett., 2003: 3, 485.

[4] Biswas, A. et al., Solid State Phenom., 2003: 94, 285.

What is claimed is:

1. A method of fabricating a surface enhanced Raman spectroscopy (SERS) substrate, comprising the step of
    forming a fractal metal-polymer nanocomposite of at least one metal and at least one polymer on a surface of a substrate, wherein the fractal metal-polymer nanocomposite comprises a plurality of nanoparticles of the at least one metal dispersed in a matrix of the at least one polymer, and wherein the plurality of nanoparticles has an average size ranging from about 10 nm to about 30 nm, and an inter-particle gap being less than about 1.5 nm; and
    applying an etching treatment to the metal-polymer nanocomposite to remove the matrix of the at least one polymer such that the plurality of nanoparticles are exposed and capable of participating light scattering in Raman spectroscopy.

2. The method of claim 1, wherein the step of forming the fractal metal-polymer nanocomposite comprises the step of performing vapor-phase codeposition of the at least one metal and the at least one polymer.

3. The method of claim 2, wherein the step of performing vapor-phase codeposition comprises the step of delivering a beam of electrons so as to simultaneously evaporate the at least one metal and the at least one polymer to form the fractal metal-polymer nanocomposite.

4. The method of claim 1, wherein the at least one metal comprises silver or gold, and wherein the at least one polymer comprises a copolymer containing tetrafluoroethylene.

5. An SERS substrate formed according to the method of claim 1.

6. The method of claim 1, wherein the etching treatment is plasma etching.

7. A surface enhanced Raman spectroscopy (SERS) substrate, comprising a nanostructure on a surface of a substrate, the nanostructure having a network of nanoparticles of a first material dispersed in a nano-scale matrix of a second material, the nanoparticles having an average size ranging from about 10 nm to about 30 nm, and an inter-particle gap being less than about 1.5 nm, wherein the nanoparticles are exposed on the nano-scale matrix, wherein the nanostructure is formed by applying an etching treatment to a nanocomposite having the nanoparticles embedded in the nano-scale matrix, and wherein the nanoparticles are capable of participating light scattering in Raman spectroscopy.

8. The SERS substrate of claim 7, wherein the first material is a metal and the second material is a polymer.

9. The SERS substrate of claim 8, wherein the first material comprises at least one of silver and gold.

10. The SERS substrate of claim 8, wherein the second material comprises a copolymer containing tetrafluoroethylene.

11. The SERS substrate of claim 8, wherein the nanocomposite of the metal and the polymer is formed by simultaneously evaporating the metal at a first evaporation rate and the polymer at a second evaporation rate different from the first evaporation rate.

12. The SERS substrate of claim 7, wherein the etching treatment is plasma etching.

* * * * *